United States Patent [19]

Maurer et al.

[11] 4,007,269
[45] Feb. 8, 1977

[54] O-ETHYL-O-n-PROPYL-O-[1-(SUBSTITUTED-PHENYL)-2-CYANO-VINYL]-THIONO-PHOSPHORIC ACID ESTERS

[75] Inventors: Fritz Maurer; Hans-Jochem Riebel; Lothar Rohe, all of Wuppertal; Ingeborg Hammann, Cologne; Bernhard Homeyer, Opladen, all of Germany

[73] Assignee: Bayer Aktiengesellschaft, Leverkusen, Germany

[22] Filed: Feb. 28, 1975

[21] Appl. No.: 554,345

[52] U.S. Cl. .................... 424/210; 260/940
[51] Int. Cl.² .................... A01N 9/36; C07F 9/165
[58] Field of Search ............ 260/940; 424/210

[56] References Cited

UNITED STATES PATENTS 3,763,285  10/1973  Riebel et al. ............ 260/940
3,775,517  11/1973  Riebel et al. ............ 260/940

*Primary Examiner*—Richard L. Raymond
*Attorney, Agent, or Firm*—Burgess, Dinklage & Sprung

[57] ABSTRACT

O-ethyl-O-n-propyl-O-[1-(substituted-phenyl)-2-cyano-vinyl]-thionophosphoric acid esters of the formula

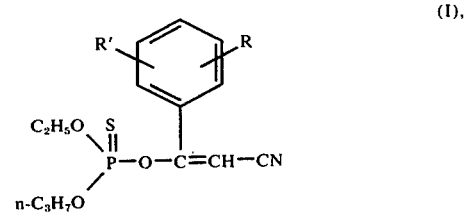

in which
R is hydrogen, $C_1$–$C_4$ alkyl, $C_1$–$C_4$ alkoxy or halogen, and
R' is $C_1$–$C_4$ alkyl, $C_1$–$C_4$ alkoxy or halogen,
which possess insecticidal and acaricidal properties.

10 Claims, No Drawings

O-ETHYL-O-n-PROPYL-O-[1(SUBSTITUTED-PHENYL)-2-CYANO-VINYL]-THIONOPHOSPHORIC ACID ESTERS

The present invention relates to and has for its objects the provision of particular new O-ethyl-O-n-propyl-O-[1-(substituted-phenyl)-2-cyano-vinyl]-thionophosphoric acid esters wherein the substituent is alkyl, alkoxy or halo, which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from German published specification DOS No. 2,030,509 that certain O,O-dialkyl-O-cyanovinyl (thiono)-phosphoric acid esters, for example O,O-diethyl-O-[1-(4'-methyl-(Compound A) or 4'-chlorophenyl)-2-cyano-vinyl]-phosphoric acid ester (Compound B) and O,O-diethyl-O-[1-(2'-methyl-(Compound C) or 2'-chloro-(Compound D) or 2',5'-dichloro-(Compound E) or 4'-methoxyphenyl)-2-cyanovinyl]-thionophosphoric acid ester (Compund F), possess insecticidal and acaricidal properties.

The present invention provides, as new compounds, the O-ethyl-O-n-propyl-O-[1-(substituted-phenyl)-2-cyanovinyl]-thionophosphoric acid esters of the general formula

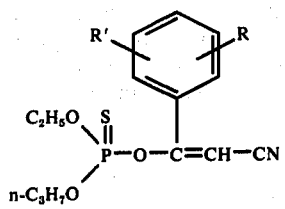

(I), in which
R is hydrogen, $C_1$–$C_4$ alkyl, $C_1$–$C_4$ alkoxy or halogen, and
R' is $C_1$–$C_4$ alkyl, $C_1$–$C_4$ alkoxy or halogen.

Preferably R is hydrogen, methyl, ethyl, methoxy, ethoxy, chlorine, bromine or fluorine and R' is methyl, ethyl, methoxy, ethoxy, chlorine, bromine or fluorine. Especially preferred are compounds in which R is hydrogen and R' is methyl, ethyl, methoxy, ethoxy, chlorine, bromine or fluorine; or in which R is methyl or ethyl and R' is methyl, ethyl, chlorine, bromine or fluorine; or in which R and R' are each selected from chlorine, bromine and fluorine.

The general formula (I) here encompasses the corresponding cis- and trans-isomers of the structures (Ia) and (Ib) below and mixtures of these components:

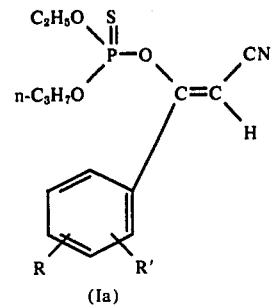

(Ia)

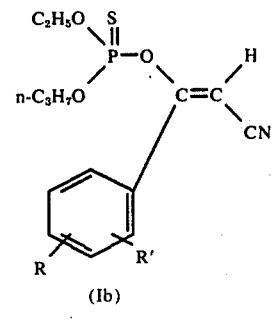

(Ib)

Surprisingly, the O-ethyl-O-n-propyl-O-vinyl-thionophosphoric acid esters (I) according to the invention are distinguished, relative to previously known compounds of analogous structure and of the same type of action, by having a better insecticidal, including soil-insecticidal, and acaricidal action, coupled with low toxicity to warm-blooded animals. The compounds according to the invention thus represent a genuine enrichment of the art.

This invention also provides a process for the preparation of an O-ethyl-O-n-propyl-O-[1-(substituted-phenyl)-2-cyanovinyl]-thionophosphoric acid ester of the formula (I), in which an O-ethyl-O-n-propylthionophosphoric acid diester halide of the general formula

(II)

in which
Hal is halogen, preferably chlorine,
is reacted with an ω-cyanoacetophenone derivative (benzoylacetonitrile) of the general formula

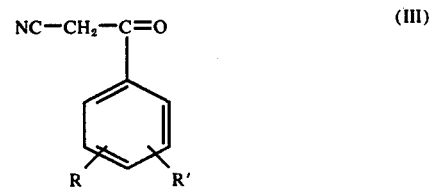

(III)

or its enol form of the general formula

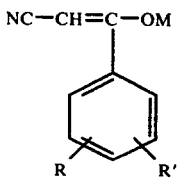 (IV), in which formulas
R and R' have the above-mentioned meanings, and
M is an alkali metal equivalent, alkaline earth metal equivalent or ammonium equivalent,
optionally in the presence of an acid acceptor and optionally in the presence of a solvent.

If, for example, O-ethyl-O-n-propyl-thionophosphoric acid diester chloride and ω-cyano-2-methylacetophenone, or the corresponding sodium salt, are used as starting materials, the course of the reaction can be represented by the following equations:

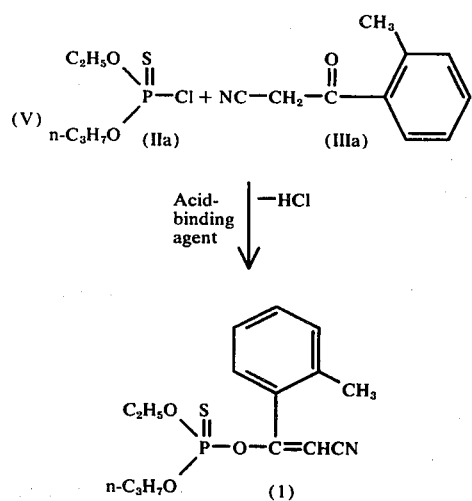

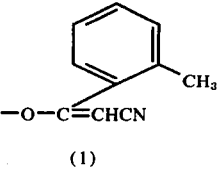

The O-ethyl-O-n-propyl-thionophosphoric acid diester chloride (II) to be used as starting material is described in the literature and is obtainable according to customary methods. Similarly, the ω-cyanoacetophenones (III) and their enol forms (IV) (see German published specification Dos No. 2,030,509) can be prepared according to known processes, for example by (a) reacting acetonitrile with phenylcarboxylic acid esters in the presence of alcoholates at elevated temperatures, optionally in a solvent, and subsequently treating the reaction mixture with acids, thus:

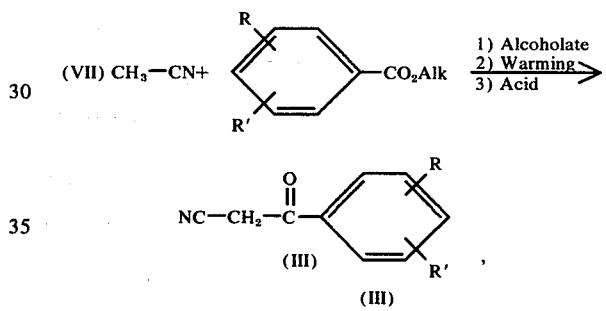

or (b) reacting the corresponding phenyl compounds with acetyl chloride in the presence of aluminum chloride, brominating the intermediate and finally replacing the bromine by the nitrile group, thus:

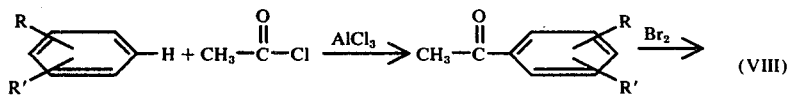

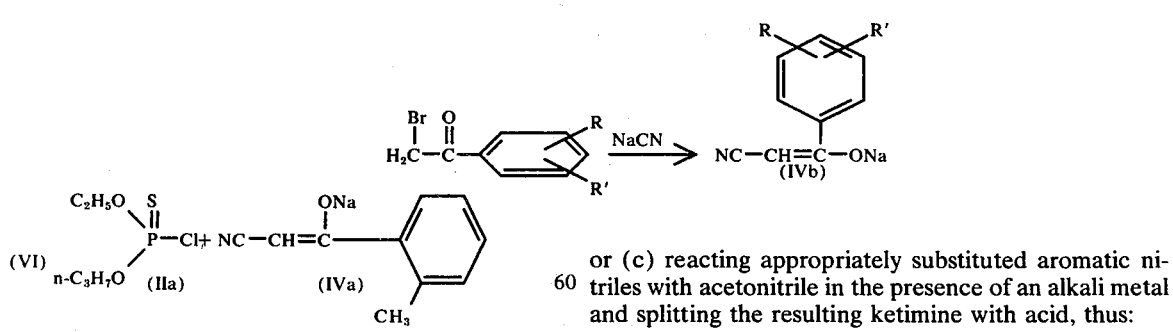

or (c) reacting appropriately substituted aromatic nitriles with acetonitrile in the presence of an alkali metal and splitting the resulting ketimine with acid, thus:

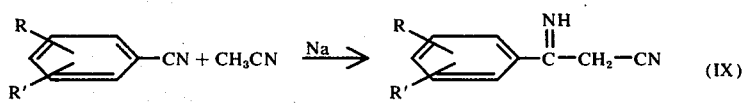

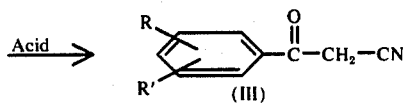

The following may be mentioned as examples of the ω-cyanoacetophenone derivatives (III) or their enol forms (IV): 2-methyl-, 2-ethyl-, 2-methoxy-, 2-ethoxy-, 2-chloro-, 2-bromo-, 2-fluoro-, 3-methyl-, 3-ethyl-, 3-methoxy-, 3-ethoxy-, 3-chloro-, 3-bromo-, 3-fluoro-, 4-methyl-, 4-ethyl-, 4-methoxy-, 4-ethoxy-, 4-chloro-, 4-bromo-, 4-fluoro-, 2,5-dichloro-, 2,5-dibromo-, 3,4-dibromo-, 2,4-dimethyl-, 2,4-diethyl-, 2-methyl-5-chloro-, 3-ethoxy-4-ethyl- and 3-bromo-4-fluoro-ω-cyano-acetophenones as well as the corresponding sodium salts of the enol forms.

The process of preparation is preferably carried out in the presence of suitable solvents and diluents. Practically all inert organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxan; ketones, for example acetone, methyl ethyl ketone, methyl isopropyl ketone and methyl isobutyl ketone; and nitriles, such as acetonitrile and propionitrile.

All customary acid-binding agents can be used as the acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at about 0° to 100°, preferably at about 20° to 55° C.

The reaction is in general allowed to take place under normal pressure.

To carry out the reaction, the starting materials are in general employed in equimolar amounts. An excess of one or other reactant in general produces no significant advantages. The reaction is preferably carried out in the presence of one of the above-mentioned solvents, optionally in the presence of an acid acceptor, at the stated temperatures. After a reaction time of one or more hours, in most cases at elevated temperature, the batch is cooled and the reaction mixture is poured into an organic solvent, for example toluene. Thereafter, the reaction mixture is worked up in the usual manner by washing with a saturated sodium bicarbonate solution and water, drying the organic phase, and evaporating the solvent.

The new compounds are obtained in the form of oils which in most cases cannot be distilled without decomposition but can be freed from the last volatile constituents by so-called "slight distillation", that is to say prolonged heating under reduced pressure to moderately elevated temperatures, and can be purified in this way. They are characterized by their refractive indexes.

As already mentioned, the O-ethyl-O-N-Propyl-O-vinylthionophosphoric acid esters according to the invention are distinguished by an outstanding insecticidal, including soilinsecticidal, and acaricidal activity. They are active against plant pest, pests harmful to health and pests of stored products and couple a very low phytotoxicity with good action against both sucking and biting insects, representative members of which are named hereinbelow.

For this reason, the compounds according to the invention can be employed successfully in plant protection and in the hygiene field and the field of protection of stored products.

To the sucking insects there belong, in the main, aphids (*Aphididae*) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the current gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (*Lepidoptera*) such as the diamond-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the biting insects are beetles (*Coleoptera*), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle *Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, *Orthoptera*, for example the house cricket (*Gryllus domesticus*); termites such as the eastern subterranean termite (*Reticulitermes flavipes*) and *Hymenoptera such as ants, for example the garden ant* (*Lasius niger*).

The *Diptera* comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (*Acarina*) there are classed, in particular, the spider mites (*Tetranychidae*) such as the two-spotted spider mite (*Tetranychus urticae*) and the European red mite (*Paratetranychus pilosus = Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the present compounds are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc. ), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vechicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Drosphila test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over a glass vessel containing 50 vinegar flies (*Drosophila melanogaster*) and covered with a glass plate.

After the specified periods of time, the destruction was determined as a percentage: 100% means that all the flies were killed.

The active compounds, their concentrations, the evaluation times and the degree of destruction can be seen from the following table:

Table 1

| | (Drosophila test) | |
|---|---|---|
| Active Compound | Active compound concentration in % | Degree of destruction in % after 1 day |
| 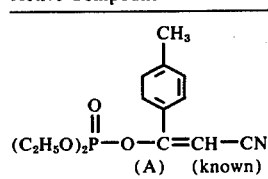<br>(A) (known) | 0.01 | 20 |

Table 1-continued

| | (Drosophila test) | |
|---|---|---|
| Active Compound | Active compound concentration in % | Degree of destruction in % after 1 day |
| 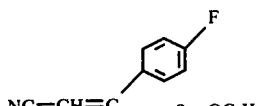<br>(5) | 0.01<br>0.001 | 100<br>100 |
| 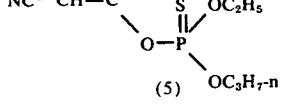<br>(2) | 0.01<br>0.001 | 100<br>100 |

EXAMPLE 2

Plutella test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed, whereas 0% means that none of the caterpillars were killed.

The active compounds, the concentrations of the active compounds, the evaluation times and the results can be seen from the following table:

Table 2

| | (Plutella test) | |
|---|---|---|
| Active Compound | Active compound concentration in % | Degree of destruction in % after 3 days |
| 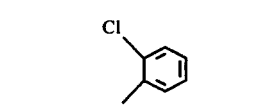<br>(B) (known) | 0.01<br>0.001 | 100<br>0 |
| 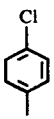<br>(F) (known) | 0.01<br>0.001 | 90<br>0 |

Table 2-continued (Plutella test)

| Active Compound | Active compound concentration in % | Degree of destruction in % after 3 days |
|---|---|---|
| (1) 2-methylphenyl derivative: NC—CH=C(Ar)—O—P(=S)(OC$_2$H$_5$)(OC$_3$H$_7$-n), Ar = 2-CH$_3$-C$_6$H$_4$ | 0.01 / 0.001 | 100 / 90 |
| (7) 2,5-dimethylphenyl derivative | 0.01 / 0.001 | 100 / 100 |
| (5) 2-fluorophenyl derivative | 0.01 / 0.001 | 100 / 100 |
| (8) 2-fluoro-5-chlorophenyl derivative | 0.01 / 0.001 | 100 / 100 |
| (2) 2-chlorophenyl derivative | 0.01 / 0.001 | 100 / 90 |
| (4) 2,5-dichlorophenyl derivative | 0.01 / 0.001 | 100 / 100 |
| (6) 2,4-dichlorophenyl derivative | 0.01 / 0.001 | 100 / 80 |

EXAMPLE 3

Myzus test (contact action)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 3

(Myzus test)

| Active Compound | Active compound concentration in % | Degree of destruction in % after 1 day |
|---|---|---|
| (F) (known): (C$_2$H$_5$O)$_2$P(=S)—O—C(=CH—CN)—C$_6$H$_4$—OCH$_3$ (para) | 0.1 / 0.01 | 98 / 50 |
| (3) 2-methoxyphenyl derivative | 0.1 / 0.01 / 0.001 | 100 / 100 / 100 |
| (1) 2-methylphenyl derivative | 0.1 / 0.01 / 0.001 | 100 / 100 / 95 |
| (7) 2,5-dimethylphenyl derivative | 0.1 / 0.01 / 0.001 | 100 / 100 / 70 |

Table 3-continued

| Active Compound | (Myzus test) Active compound concentration in % | Degree of destruction in % after 1 day |
|---|---|---|
| (7) F-C6H3(Cl)-C(=CH-NC)-O-P(=S)(OC2H5)(OC3H7-n) | 0.1<br>0.01<br>0.001 | 100<br>100<br>100 |
| (8) Cl-C6H4-C(=CH-NC)-O-P(=S)(OC2H5)(OC3H7-n) | 0.1<br>0.01<br>0.001 | 100<br>100<br>95 |
| (2) Cl-C6H3(Cl)-C(=CH-NC)-O-P(=S)(OC2H5)(OC3H7-n) | 0.1<br>0.01<br>0.001 | 100<br>100<br>90 |
| (4) | | |
| (6) Cl-C6H3(Cl)-C(=CH-NC)-O-P(=S)(OC2H5)(OC3H7-n) | 0.1<br>0.01<br>0.001 | 100<br>100<br>95 |

EXAMPLE 4

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed whereas 0% means that none of the spider mites were killed.

The active compounds, the concentrations of the active compounds, the evaluation times and the results can be seen from the following table:

Table 4

| Active Compound | (Tetranychus test) Active compound concentration in % | Degree of destruction in % after 2 days |
|---|---|---|
| (C) (known) (C2H5O)2P(=S)-O-C(CH3)=CH-CN (o-tolyl) | 0.1<br>0.01 | 90<br>0 |
| (E) (known) (C2H5O)2P(=S)-O-C(=CH-CN)-C6H3(Cl)(Cl) | 0.1<br>0.01 | 60<br>0 |

Table 4-continued

| (Tetranychus test) | | |
|---|---|---|
| Active Compound | Active compound concentration in % | Degree of destruction in % after 2 days |
| 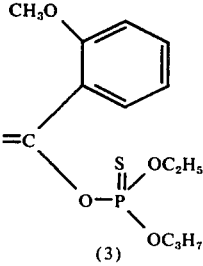 (3) | 0.1<br>0.01 | 98<br>95 |
| 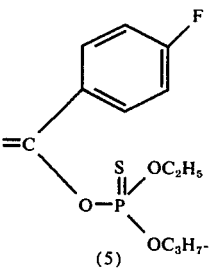 (5) | 0.1<br>0.01 | 100<br>98 |
| 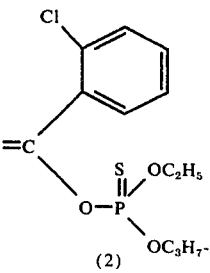 (2) | 0.1<br>0.01 | 95<br>90 |
| 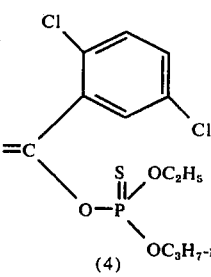 (4) | 0.1<br>0.01 | 99<br>95 |

EXAMPLE 5

Critical concentration test/soil insects
Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance; only the amount by weight of active compound per unit volume of soil, which is given in ppm (for example mg/l), was decisive. The soil was filled into pots and the pots were left to stand at room temperature. After 24 hours, the test insects were introduced into the treated soil and after a further 48 hours the degree of effectiveness of the active compound was determined in % by counting the dead and the live test insects. The degree of destruction is 100% if all test insects had been killed and is 0% if just as many test insects were still alive as in the case of the control.

The active compounds, the amounts used and the results can be seen from the table which follows:

Table 5

(Soil insecticide test/*Tenebrio molitor* larvae in the soil)

| Active Compound | Degree of destruction in % at an active compound concentration of 20 ppm |
|---|---|
| 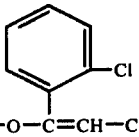 (D) (known) $(C_2H_5O)_2\overset{\underset{\|}{S}}{P}-O-C=CH-CN$ with o-Cl phenyl | 0 |
| 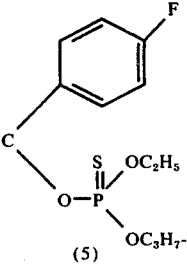 (5) with 4-F phenyl, $NC-CH=C$, $O-\overset{\underset{\|}{S}}{P}(OC_2H_5)(OC_3H_7\text{-}n)$ | 100 |
| 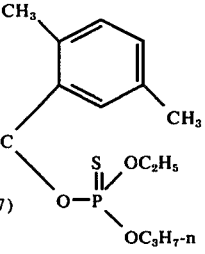 (7) with 2,5-dimethylphenyl | 100 |
| 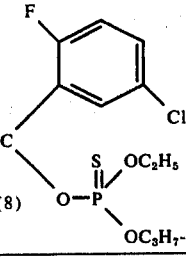 (8) with 2-F, 5-Cl phenyl | 100 |

EXAMPLE 6

Critical concentration test/soil insects
Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance; only the amount by weight of active compound per unit volume of soil, which is given in ppm (for example mg/l) was decisive. The soil was filled into pots and the pots were left to stand at room temperature. After 24 hours, the test insects were introduced into the treated soil and after a further 48 hours the degree of effectiveness of the active compound was determined in % by counting the dead and the live test insects. The degree of destruction is 100% if all test insects had been killed and is 0% if just as many test insects were still alive as in the case of the control.

The active compounds, the amounts used and the results can be seen from the table which follows:

Table 6

(Soil insecticide test/*Phorbia antiqua* larvae in the soil)

| Active Compound | Degree of destruction in % at an active compound concentration of 20 ppm |
|---|---|
| 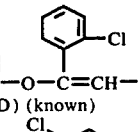 (D) (known) $(C_2H_5O)_2\overset{\underset{\|}{S}}{P}-O-C=CH-CN$ with o-Cl phenyl | 0 |
| 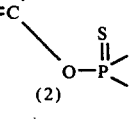 (2) with 2-Cl phenyl | 100 |
| 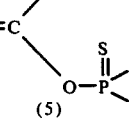 (5) with 4-F phenyl | 100 |
| 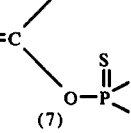 (7) with 2,5-dimethylphenyl | 100 |
| 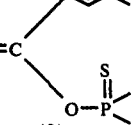 (8) with 2-F, 5-Cl phenyl | 100 |

The process of this invention is illustrated by the following preparative Examples.

EXAMPLE 7

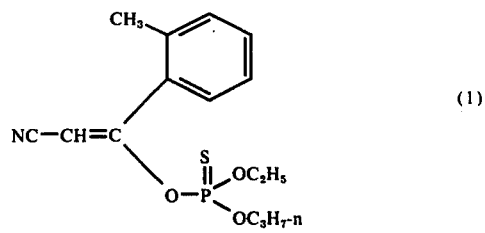

(1)

20.2 g (0.1 mole) of O-ethyl-O-n-propyl-thionophosphoric acid diester chloride were added dropwise to a mixture of 15.9 g (0.1 mole) of ω-cyano-2-methylacetophenone, 14.2 g (0.11 mole) of potassium carbonate and 150 ml of acetonitrile. The reaction mixture was then warmed to 50° C for 3 hours and cooled, and the batch was poured into 300 ml of toluene. The toluene solution was washed with saturated sodium bicarbonate solution and water and dried over sodium sulphate, and the solvent was then stripped off under reduced pressure. 28 g (86% of theory) of O-ethyl-O-n-propyl-O-[1-(2'-methylphenyl)-2-cyanovinyl]-thionophosphoric acid ester were obtained as a yellow oil having a refractive index $n_D^{25}$ of 1.5320.

The following compounds could be prepared analogously:

A solution of 10.8 g of sodium cyanide in 20 ml of water and 20 ml of ethanol was added dropwise, while stirring, to 26.8 g (0.1 mole) of 2',5'-dichloro-2-bromoacetophenone (prepared from p-dichlorobenzene and acetyl chloride by the Friedel-Crafts method, followed by bromination in ether) in 30 ml of ethanol, during which the temperature of the mixture rose to 50° C. The batch was stirred for a further 15 minutes and cooled to 10° C, and the salt which had precipitated was thoroughly suction-drained. It was rinsed with ether and dried for 5 hours at 100° to 110° C under reduced pressure. 19.5 g (83% of theory) of a beige

| Compound No. | Formula | Refractive index | Yield (% of theory) |
|---|---|---|---|
| 2 | NC—CH=C(Cl-C₆H₄)(O-P(S)(OC₂H₅)(OC₃H₇-n)) | $n_D^{23}$: 1.5427 | 81 |
| 3 | NC—CH=C(CH₃O-C₆H₄)(O-P(S)(OC₂H₅)(OC₃H₇-n)) | $n_D^{25}$: 1.5350 | 77 |

EXAMPLE 8 a) 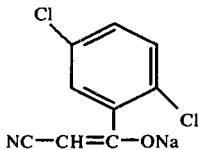

powder of melting point 300° C were thus obtained.

Sodium salts of the following ω-cyanoacetophenones, or the free ω-cyanoacetophenones by rinsing of the salt with aqueous HCl, were also obtained analogously:

| Formula | Yield (% of theory) | Physical properties (boiling point, °C/mm Hg, or melting point, °C) |
|---|---|---|
| NC—CH₂—CO—C₆H₄—Cl | 68 | 129° C |
| NC—CH₂—CO—C₆H₄(Cl) | 53 | 75–78° C |
| NC—CH₂—CO—C₆H₄(Cl) | 43 | 125° C |

-continued

| Formula | Yield (% of theory) | Physical properties (boiling point, °C/mm Hg, or melting point, °C) |
|---|---|---|
| NC—CH₂—CO—C₆H₄(Br) (2-Br) | 35 | 150–160° C/44 mm Hg |
| NC—CH₂—CO—C₆H₄—CH₃ (4-CH₃) | 33 | 100° C |
| NC—CH₂—CO—C₆H₄—CH₃ (3-CH₃) | 49 | 72° C |
| NC—CH₂—CO—C₆H₄—CH₃ (2-CH₃) | 37 | 84–85° C |
| NC—CH=C(ONa)—C₆H₄—OCH₃ (4-OCH₃) | 77 | — |
| NC—CH₂—CO—C₆H₄—OCH₃ (3-OCH₃) | 71 | 88° C |
| NC—CH₂—CO—C₆H₄—OCH₃ (2-OCH₃) | 50 | 67° C |
| NC—CH=C(ONa)—C₆H₃(Cl)₂ (2,4-Cl₂) | 51 | — |
| NC—CH=C(ONa)—C₆H₄—F (4-F) | 75 | 284° C (decomposition) |
| NC—CH=C(ONa)—C₆H₄—Br (4-Br) | 82 | — |
| NC—CH=C(ONa)—C₆H₃(Br)₂ (3,4-Br₂) | 37 | 272° C (decomposition) |

-continued

| Formula | Yield (% of theory) | Physical properties (boiling point, ° C/mm Hg, or melting point, ° C) |
|---|---|---|
| 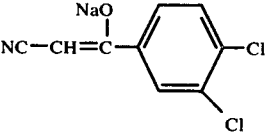 | 77 | — |
| 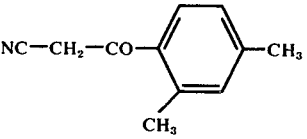 | 20 | 74° C |
| 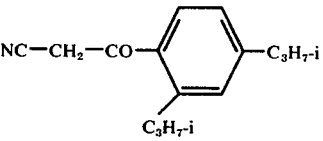 | 18 | 56° C |
| 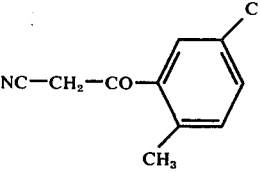 | 22 | 71° C | b)

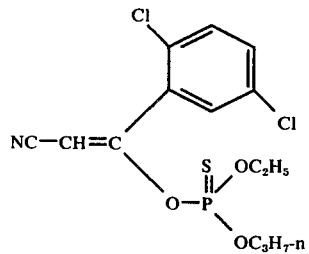

(4)

20.2 g (0.1 mole) of O-ethyl-O-n-propyl-thionophosphoric acid diester chloride were added dropwise to a solution of 23.6 g (0.1 mole) of the sodium salt of ω-cyano-2,5-dichloroacetophenone, produced in (a), in 200 ml of acetonitrile. The reaction mixture was warmed to 50° C for 3 hours and cooled, and the batch was poured into 300 ml of toluene. The toluene solution was washed with saturated sodium bicarbonate solution and water and dried over sodium sulfate, and the solvent was then stripped off under reduced pressure. 28.5 g (75% of theory) of O-ethyl-O-n-propyl-O-[1-(2',5'-dichlorophenyl)-2-cyano-vinyl]-thionophosphoric acid ester were obtained as an oil having a refractive index $n_D^{24}$ of 1.5245.

The following compounds were prepared analogously:

| Compound No. | Formula | Refractive index | Yield (% of theory) |
|---|---|---|---|
| 5 | 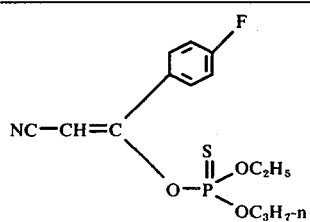 | $n_D^{23}$: 1.5190 | 76 |
| 6 | 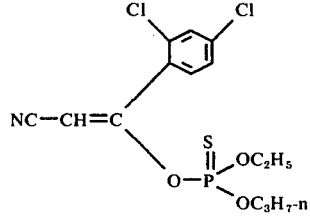 | $n_D^{23}$: 1.5407 | 58 |

-continued

| Compound No. | Formula | Refractive index | Yield (% of theory) |
|---|---|---|---|
| 7 | 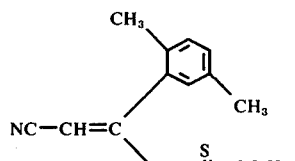 | $n_D^{22}$: 1.5272 | 71 |
| 8 | 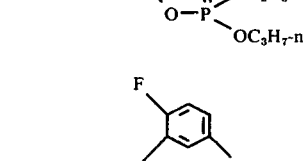 | $n_D^{24}$: 1.5372 | 43 |

Other compounds which can be similarly prepared include:

O-ethyl-O-n-propyl-O-[1-(2'-methyl-5'-bromophenyl)-2-cyano-vinyl]-thionophosphoric acid ester,
O-ethyl-O-n-propyl-O-[1-(3'-chloro-4'-methoxyphenyl)-2-cyano-vinyl]-thionophosphoric acid ester,
O-ethyl-O-n-propyl-O-[1-(3'-butoxy-4'-methylphenyl)-2-cyano-vinyl]-thionophosphoric acid ester,
O-ethyl-O-n-propyl-O-[1-(2'-methoxy-5'-isopropoxyphenyl)-2-cyano-vinyl)-thionophosphoric acid ester, and the like.

It will be appreciated that the instant specification and examples are set forth by way of illustration and not limitation, and that various modifications and changes may be made without departing from the spirit and scope of the present invention.

What is claimed is:

1. An O-ethyl-O-n-propyl-O-[1-(substituted-phenyl)-2-cyano-vinyl]-thionophosphoric acid ester of the formula

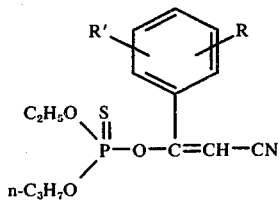

in which
R is hydrogen, $C_1$–$C_4$ alkyl, $C_1$–$C_4$ alkoxy or halogen, and
R' is $C_1$–$C_4$ alkyl, $C_1$–$C_4$ alkoxy or halogen.

2. A compound according to claim 1, in which R is hydrogen, methyl, ethyl, methoxy, ethoxy, chlorine, bromine or fluorine and R' is methyl, ethyl, methoxy, ethoxy, chlorine, bromine or fluorine.

3. The compound according to claim 1 wherein such compound is O-ethyl-O-n-propyl-O-[1-(2'-methylphenyl)-2-cyanovinyl]-thionophosphoric acid ester of the formula

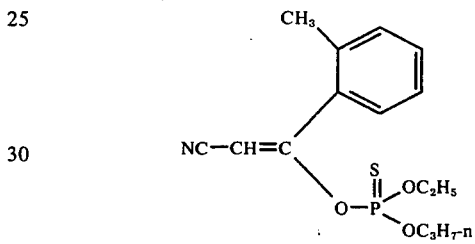

4. The compound according to claim 1 wherein such compound is O-ethyl-O-n-propyl-O-[1-(2'-chlorophenyl)-2-cyano-vinyl]-thionophosphoric acid ester of the formula

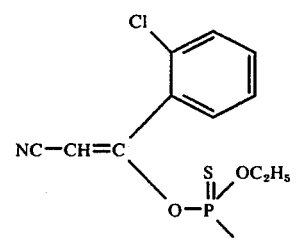

5. The compound according to claim 1 wherein such compound is O-ethyl-O-n-propyl-O-[1-(2',5'-dichlorophenyl)-2-cyano-vinyl]-thionophosphoric acid ester of the formula

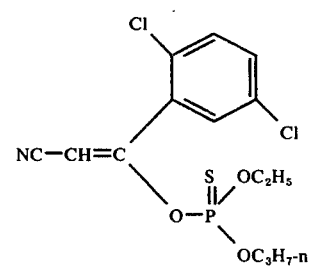

6. The compound according to claim 1 wherein such compound is O-ethyl-O-n-propyl-O-[1-(2',4'-dichlorophenyl)-2-cyano-vinyl]-thionophosphoric acid ester of the formula

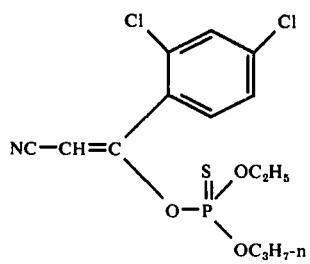

7. The compound according to claim 1 wherein such compound is O-ethyl-O-n-propyl-O-[1-(2'-fluoro-5'-chlorophenyl)-2-cyano-vinyl]-thionophosphoric acid ester of the formula

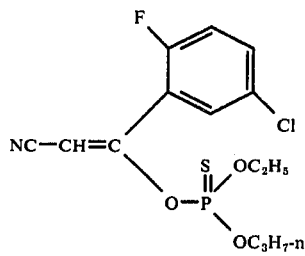

8. An insecticidal or acaricidal composition containing as active ingredient an insecticidally or acaricidally effective amount of a compound according to claim 1 in admixture with a diluent.

9. A method of combating insects or acarids which comprises applying to the insects or acarids or to a habitat thereof an insecticidally or acaricidally effective amount of a compound according to claim 1.

10. The method according to claim 9 in which said compound is

O-ethyl-O-n-propyl-O-[1-(2'-methylphenyl)-2-cyano-vinyl]-thionophosphoric acid ester,
O-ethyl-O-n-propyl-O-[1-(2'-chlorophenyl)-2-cyano-vinyl]-thionophosphoric acid ester,
O-ethyl-O-n-propyl-O-[1-(2',5'-dichlorophenyl)-2-cyano-vinyl]-thionophosphoric acid ester,
O-ethyl-O-n-propyl-O-[1-(2',4'-dichlorophenyl)-2-cyano-vinyl]-thionophosphoric acid ester, or
O-ethyl-O-n-propyl-O-[1-(2'-fluoro-5'-chlorophenyl)-2-cyano-vinyl]-thionophosphoric acid ester.

* * * * *